United States Patent [19]

Uchida et al.

[11] Patent Number: 4,965,018
[45] Date of Patent: Oct. 23, 1990

[54] OPTICALLY ACTIVE PYRIDYLETHANOL DERIVATIVE

[75] Inventors: Manabu Uchida, Kanagawa; Naoyuki Yoshida; Masakazu Kaneoya, both of Chiba, all of Japan

[73] Assignee: Chisso Corporation, Ohsaka, Japan

[21] Appl. No.: 326,795

[22] Filed: Mar. 21, 1989

[30] Foreign Application Priority Data

Apr. 6, 1988 [JP] Japan .................................. 63-84671

[51] Int. Cl.$^5$ .................... C09K 19/34; C07D 403/00; C07D 211/70
[52] U.S. Cl. .......................... 252/299.61; 252/299.63; 252/299.5; 252/299.66; 544/296; 544/298; 544/316; 544/333; 546/342; 546/339
[58] Field of Search ........... 252/299.61, 299.5, 299.01; 350/350 R, 350 S; 544/296, 298, 316, 333; 546/342, 339

[56] References Cited

U.S. PATENT DOCUMENTS

| | | | |
|---|---|---|---|
| 4,744,918 | 5/1988 | Heppke et al. | 252/299.61 |
| 4,764,619 | 8/1988 | Gunjima et al. | 252/299.01 |

FOREIGN PATENT DOCUMENTS

| | | | |
|---|---|---|---|
| 217240 | 4/1987 | European Pat. Off. | 252/299.01 |
| 3534777 | 4/1987 | Fed. Rep. of Germany | 252/299.01 |
| 3606312 | 9/1987 | Fed. Rep. of Germany | 252/299.01 |
| 60-38346 | 2/1985 | Japan | 252/299.01 |
| 61-174294 | 8/1986 | Japan | 252/299.01 |
| 8705012 | 8/1987 | World Int. Prop. O. | 252/299.01 |

OTHER PUBLICATIONS

Takeshita, M. et al., Heterocycles, vol. 26, No. 12, pp. 3051–3054 (1987).

*Primary Examiner*—John S. Maples
*Assistant Examiner*—Richard Treanor
*Attorney, Agent, or Firm*—Wenderoth, Lind & Ponack

[57] ABSTRACT

A novel optically active pyridylethanol derivative having a high twistability and also a superior temperature characteristic is provided, which derivative is expressed by the formula

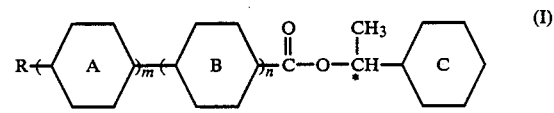

wherein R is an alkyl group of alkoxy group each of 1 to 20 carbon atoms or hydrogen atom, m and n each represent 0 or 1,

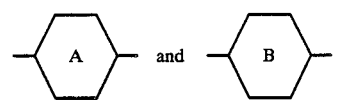

each independently represent

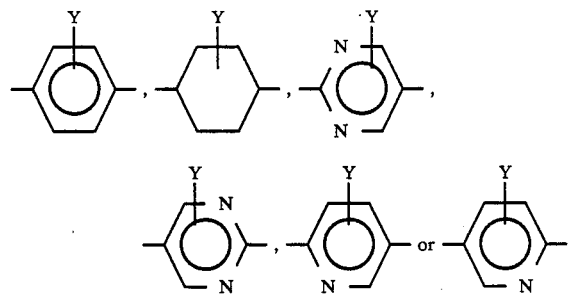

wherein Y is any one of H, halogen atom or CN and

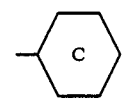

is a pyridine ring the N atom of which may be present at an optionally chosen site thereof.

8 Claims, No Drawings

OPTICALLY ACTIVE PYRIDYLETHANOL DERIVATIVE

BACKGROUND OF THE INVENTION

1. Field of the Invention

This invention relates to a novel optically active pyridylethanol derivative and a liquid crystal composition containing the same.

2. Description of the Related Art

As to liquid crystal display elements, their use applications have been rapidly broadened due to improvements in circuits, driving modes and cell preparation techniques and particularly due to improvement in characteristics of liquid crystal compositions filled in the elements. However, current liquid crystal display elements still have a number of drawbacks to be overcome, such as narrow angle of view, inferior contrast, low response rate, still yet small display capacity, deterioration in the display quality due to change in ambient temperature, etc. Among these, the deterioration in the display quality due to change in ambient temperature is said to originate in the temperature change of threshold voltage (Vth).

In recent years, as a means usually employed, there has been known a method of adding a slight quantity of an optically active substance to a liquid crystal composition to thereby suppress the reverse twist of the liquid crystal molecule and impart a right-handed or left-handed helical structure to the liquid crystal molecule to retain the display quality. Hence, in the case of TN (Twisted Nematic) mode display elements and recently proposed SBE (Super twisted Birefringence Effect) mode display elements, etc., the above-mentioned method can have an advantageous influence. However, if the twistability of the optically active substance to be added as a dopant is too low, it is necessary to add the substance in a relatively high concentration in order to obtain a required pitch; hence it is noted that this has an influence upon other substance parameters. Thus, an optically active substance having a high twistability, i.e. when added to liquid crystals, having a capability of exhibiting a shorter pitch in the same quantity added, has been long awaited. For example, in the case of CB-15 made by BDH Company or compounds disclosed in Japanese patent application laid-open Nos. Sho 62-81354/1987 and Sho 62-81355/1987, when these compounds are added in an amount only one percent by weight to nematic liquid crystal compositions, they have a capability of exhibiting a pitch of about 10 um; hence they can be practically usable, optically active substances in a certain sense.

However, generally known optically active substances including the above-mentioned compounds generally vary the pitch with temperature change and often have an undesirable influence. For example, in the case of SBE mode, the intrinsic pitch P of the liquid crystal composition varies with temperature change and thereby the ratio of the intrinsic pitch P of the liquid crystal composition to the cell thickness d of the display element (P/d) also varies. P/d is usually 2 or less, but if it exceeds 2, 270° twist changes to 90° twist. Further, from the aspect of improvement in the increase of display capacity, it is necessary to improve the steepness of change in the transmittance in the case where voltage is being impressed onto display elements. G. Bauer and W. Fehlenback reported a calculation result that 270° twist notably improves the steepness (the 15th Freiburg liquid crystal symposium (1985), but even in this case, it is necessary to be free the composition of change in the intrinsic pitch dependent on temperature change.

As a method for solving this problem, it has been reported in recent years that when an optically active compound having a negative temperature characteristic, i.e. a substance the intrinsic pitch of which is reduced with temperature rise, is blended with an optically active compound having a positive temperature characteristic, i.e. a substance the intrinsic pitch of which is increased with temperature rise, each in an adequate quantity, then a composition free of change in the intrinsic pitch depending on temperature is obtained(Japanese patent application laid-open No. Sho 63-22893/1988).

However, since two kinds of optically active compounds, i.e. a substance having a positive temperature characteristic and that having a negative one, should be blended together, this requires complicated steps such as a search for adequate blending ratios.

Furthermore, any of currently reported substances having a negative temperature characteristic have a low twistability; hence in order to obtain a required pitch, it is necessary to add the substances in a considerably high concentration so that this appears to have various bad influences. Thus, in order to solve such various problems, there has been desired a substance having a short pitch and yet having a superior temperature characteristic, in short, free of change in the pitch with temperature change.

SUMMARY OF THE INVENTION

The object of the present invention is to provide an optically active compound having characteristics required for realizing liquid crystal compositions having suitable characteristics, i.e. an optically active compound having a high twistability and also a superior temperature characteristic.

The present invention in a first aspect resides in an optically active pyridylethanol derivative expressed by the formula

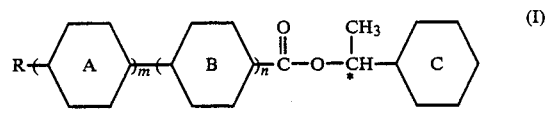

wherein R represents an alkyl group or an alkoxy group each of 1 to 20 carbon atoms or hydrogen atom, m and n each represent 0 or 1,

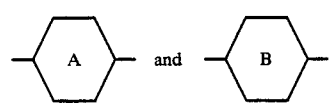

each independently represent

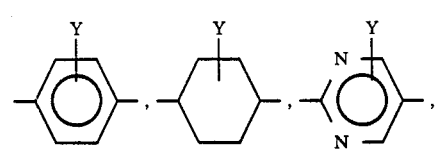

-continued

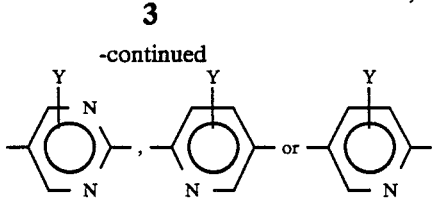

wherein Y represents any one of hydrogen atom, a halogen atom and a cyano group, and

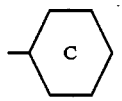

represents a pyridine ring the nitrogen atom of which may be present at an optionally chosen site thereof.

Among the compounds of the formula (I), those wherein m represents 1, n represents 1 and either one of

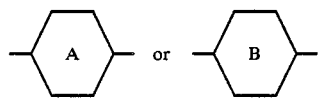

represents

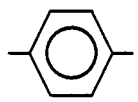

are preferred, and those wherein both of

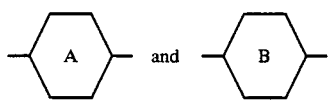

represent

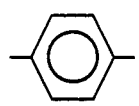

are particularly preferred.

The present invention in a second aspect resides in a liquid crystal composition comprising at least two components at least one of which is the above-mentioned optically active compound.

The present invention in a third aspect resides in an electrooptical element using the above-mentioned liquid crystal composition.

DETAILED DESCRIPTION OF PREFERRED EMBODIMENTS

The superior characteristics of the compound of the present invention originate in the following core:

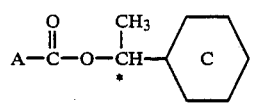

wherein ring C represents a pyridine ring the nitrogen atom of which may be present at an optional site, and in the absence of this core, no superior characteristic can be exhibited. In other words, when the above-mentioned core is contained in the molecular structure, superior characteristics can be exhibited. Thus, it goes without saying that A in the above formula may take various structures. Further, since the compound of the present invention has a high twistability, the quantity thereof required for obtaining a chiral liquid crystal composition having an optimized twisted structure can be slight. Thus, it is possible to blend the compound with various kinds of liquid crystal substances. Examples of such liquid crystal substances are liquid crystal compounds exhibiting nematic liquid crystal phase, represented by Schiff's bases, biphenyls, phenylcyclohexanes, phenylpyridines, phenylpyrimidines, phenyldioxanes, cyclohexylbiphenyls, cinnamic acid esters, phenyl esters, etc. and liquid crystal compositions consisting of constituents optionally chosen from the foregoing.

Preparation of the compound:

The compound of the formula (I) of the present invention can be preferably prepared through the following route:

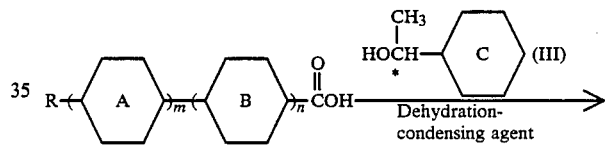

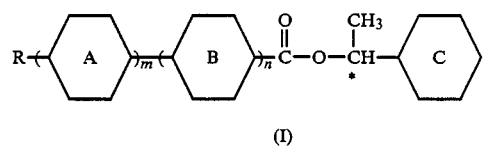

In the above formulas, m, n, R,

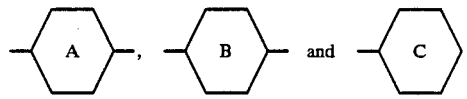

are as defined above.

Namely, various kinds of carboxylic acids expressed by the formula (II) are reacted with an optically active pyridylethanol expressed by the formula (III), i.e. optically active 1-(2-pyridyl)ethanol, optically active 1-(3-pyridyl)ethanol or optically active 1-(4-pyridyl)ethanol, in the presence of a dehydration-condensing agent to carry out a dehydration-condensation reaction, whereby it is possible to obtain a compound of the formula (I) of the present invention.

Further, the compound of the formula (I) can also prepared through the following route:

$$(II) \longrightarrow R\!-\!(A)_{\!m}\!-\!(B)_{\!n}\!-\!\overset{O}{\underset{\|}{C}}\!.Cl \xrightarrow[\text{Basic catalyst}]{HOCH\!-\!(C) \;(III)} (I)$$

$$(IV)$$

Namely, carboxylic acid halides such as carboxylic acid chlorides expressed by the formula (IV) can be derived from various carboxylic acid expressed by the formula (II), followed by reacting the chlorides as the halides with an optically active compound expressed by the formula (III) in the presence of a basic catalyst such as pyridine to prepare the compound of the formula (I).

Further, the optically active pyridylethanols may be prepared according to various processes. For example, a process of subjecting a pyridylethanol as a racemate to a stereoselective ester exchange in the presence of a hydrolase (Japanese patent application No. Sho 62-212674/1987), a process of subjecting acetylpyridine to an asymmetric reduction in the presence of a reductase (M. R. Uskokovic et al, J.A.C.S., 101, 6742 (1979), etc. are particularly useful.

Further, examples of the carboxylic acids of the formula (II) as a raw material are as follows:
benzoic acids represented by
benzoic acid,
4-alkylbenzoic acids,
2-fluoro-4-alkylbenzoic acids,
4-alkoxybenzoic acids,
3-cyano-4-alkoxybenzoic acids and
3-fluoro-4-alkoxybenzoic acids;
cyclohexylcarboxylic acids represented by
cyclohexylcarboxylic acid,
4-alkylcyclohexylcarboxylic acids and
4-alkoxycyclohexylcarboxylic acids;
pyridine carboxylic acids which are easily prepared according to the method disclosed in Pavluchenko et al, Mol. Cryst. Liq. Cryst., 37, 35 (1976) such as
5-pyridinecarboxylic acid,
2-alkylpyridine-5-carboxylic acids,
2-alkoxypyridine-5-carboxylic acids,
2-pyridinecarboxylic acid,
5-alkylpyridine-2-carboxylic acids and
5-alkoxypyridine-2-carboxylic acids;
pyrimidinecarboxylic acids represented by
5-pyrimidinecarboxylic acid,
2-alkylpyrimidine-5-carboxylic acids,
2-alkoxypyrimidine-5-carboxylic acids,
2-pyrimidinecarboxylic acid,
5-alkylpyrimidine-2-carboxylic acids and
5-alkoxypyrimidine-2-carboxylic acids;
phenylcarboxylic acids represented by
4-biphenylcarboxylic acid,
4-alkylbiphenyl-4'-carboxylic acids,
3-fluoro-4-alkylbiphenyl-4'-carboxylic acids,
3-cyano-4-alkylbiphenyl-4'-carboxylic acids,
3-fluoro-4-alkoxybiphenyl-4'-carboxylic acids and
3-cyano-4-alkoxybiphenyl-4'-carboxylic acids;
cyclohexylbenzoic acids which can be easily prepared according to the method disclosed in T. Szenzucinski et al, Mol. Cryst. Liq. Cryst., 88, 55 (1982) such as
4-cyclohexylbenzoic acid,
4-(4-alkylcyclohexyl)benzoic acids,
4-(4-alkoxycyclohexyl)benzoic acids,
4-phenylcyclohexylcarboxylic acid,
4-(4-alkylphenyl)cyclohexylcarboxylic acids,
4-(4-alkoxyphenyl)cyclohexylcarboxylic acids and
2-phenylpyrimidine-5-carboxylic acid;
2-phenyl-5-cyano-pyrimidines which can be easily prepared according to the method disclosed in Japanese patent publication No. Sho 55-6631 and 5-phenyl-2-cyano-pyrimidines which can be easily prepared according to H. Zaschke, Z. Chem. 17, 333 (1977) such as
2-(alkylphenyl)pyrimidine-5-carboxylic acids,
2-(4-alkoxyphenyl)pyrimidine-5-carboxylic acids,
2-(3-fluoro-4-alkoxyphenyl)pyrimidine -5-carboxylic acids,
2-(3-cyano-4-alkoxyphenyl)pyrimidine-5-carboxylic acids,
5-(alkylphenyl)pyrimidine-2-carboxylic acids,
5-(4-alkoxyphenyl)pyrimidine-2-carboxylic acids,
5-(3-fluoro-4-alkoxyphenyl)pyrimidine-2-carboxylic acids and
5-(3-cyano-4-alkoxyphenyl)pyrimidine-2-carboxylic acis; and
phenylpyridinecarboxylic acids represented by
2-(3-cyano-4-alkoxyphenyl)pyridine-5-carboxylic acids,
5-phenylpyridine-2-carboxylic acids,
5-(alkylphenyl)pyridine-2-carboxylic acids,
5-(4-alkoxyphenyl)pyridine-2-carboxylic acids,
5-(3-fluoro-4-alkoxyphenyl)pyridine-2-carboxylic acids and
5-(3-cyano-4-alkoxyphenyl)pyridine-2-carboxylic acids.

The advantageous effects of the present invention will be described below.

(1) When the compound of the present invention is used as a dopant, it induces a highly twisted structure when a slight quantity thereof is added. As shown in Example 2 mentioned later, when an optically active compound of the present invention is added in an amount one percent by weight to a liquid crystal composition having no twisted structure, the resulting pitch is as short as 4.6 um at 25° C.; hence it is possible to prepare a liquid crystal composition having a twisted structure, i.e. a chiral liquid crystal composition, optimized by adding a small quantity thereof. It is seen that this is a surprising specific feature, taking into account the case of optically active compounds currently known as dopants; for example, C-15 made by BDH Company has a pitch of 63 um and even CB-15 has a pitch of only 10 um.

(2) The liquid crystal composition containing the compound of the present invention has a good temperature characteristic, i.e. its pitch is unchanged with temperature change. As shown in Example 2, the temperature characteristic $\delta P$ is as good as $\pm 0$ at $t_1 = 20°$ C. and $t_2 = 40°$ C.; hence it is unnecessary to employ the generally known process of blending a substance having a positive temperature characteristic with a substance having a negative temperature characteristic so that it is possible to easily provide chiral compositions.

(3) When the compound of the present invention is added to a compound or composition having a smectic C phase, it is possible to induce a chiral smectic C phase.

(4) The compound of the formula (I) of the present invention includes single-ring compounds ($m=0$ and $n=0$ in the formula (I)) having low melting points, two-ring compounds ($m=1$ and $n=0$ or $m=0$ and $n=1$) having somewhat high melting points, and three-ring compounds ($m=1$ and $n=1$) having high melting points so that it is possible to optionally obtain substances having a broad range of melting points; hence when the compound of the present invention is added as a modifier for the twisted pitch of liquid crystal compositions, it is possible to optionally choose m and n of the formula (I) depending upon a level of the temperature region of the nematic phase of liquid crystal compositions used, and thereby provide a pitch-modifier suitable to that level.

The present invention will be described in more detail by way of Examples, but it should not be construed to be limited thereto.

EXAMPLE 1

Preparation of (S)-4-octyloxybiphenyl-4'-carboxylic acid-1-(3-pyridyl)ethyl ester (i) Preparation of (R,S)-1-(3-pyridyl)ethanol A suspension of sodium borohydride (2.4 g) in isopropyl alcohol (50 ml) was cooled down to 0° C., followed by dropwise adding a solution of 3-acetylpyridine (20 g) dissolved in isopropyl alcohol (50 ml), agitating the mixture for 6 hours, thereafter adding 1N HCl (100 ml) and CHCl₃ (100 ml), separating the resulting organic layer and concentrating the layer to obtain a liquid (20.3 g). The NMR spectra of this substance accorded with that of the captioned compound.

(ii) Preparation of (S)-1-(3-pyridyl)ethanol 1-(3-Pyridyl)ethanol (8.9 g), tributyrin (24.0 g) and an enzyme (Lipase CES made by Amano Seiyaku K. K.) (3.6 g) were agitated at 37° C. for 190 hours, followed by filtering off the enzyme and subjecting the filtrate to silica gel column chromatography using toluene as solvent to obtain (S)-1-(3-pyridyl)ethanol (3.0 g). According to a high-speed liquid chromatography using an optical resolution column (CHIRAL CEL OB, trademark of product made by Daicel Co., Ltd.), its optical purity was 80% ee or higher.

(iii) Preparation of (S)-4-octyloxybiphenyl-4'-carboxylic acid-1-(3-pyridyl)ethyl ester (a compound of the formula (I) wherein m=n=1,

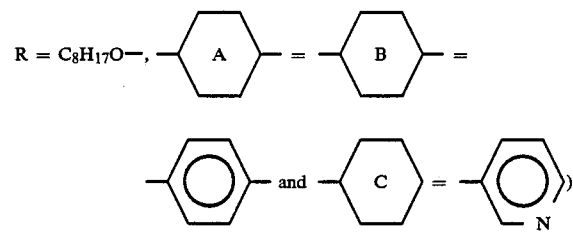

(S)-1-(3-pyridyl)ethanol (2.0 g) prepared in the above item (ii), 4-octyloxybiphenyl-4'-carboxylic acid (5.3 g), dicyclohexylcarbodiimide (5.7 g) and dimethylaminopyridine (0.2 g) were dissolved in methylene chloride (100 ml), followed by agitating the solution for 15 hours, thereafter filtering off insolubles, washing the filtrate with water, concentrating it and recrystallizing from a mixed solvent of heptane-toluene to obtain (S)-4-octyloxybiphenyl-4'-carboxylic acid-1-(3-pyridyl)ethyl ester (0.5 g). M.P.: 77.5–78.5° C. Specific angle of rotation $[\alpha]_D^{25} = +95°$ (c=1.0, CHCl₃). Further, the structure of this product was confirmed according to NMR spectra and the product accorded with the captioned compound.

EXAMPLE 2 (USE EXAMPLE 1)

To a nematic liquid crystal composition (commercially available ZLI-1132 made by Merck Company) was added a compound of Example 1 of the present invention

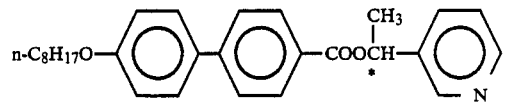

in an amount of 1% by weight to prepare a chiral nematic liquid crystal composition, followed by filling this composition in a wedge type cell subjected to a parallel treatment and observing the resulting cell under a polarizing microscope. As a result, the following helical pitches were observed:

| Temperature (°C) | 20 | 25 | 30 | 40 | 50 | 60 |
|---|---|---|---|---|---|---|
| Pitch length (μm) | 4.6 | 4.6 | 4.6 | 4.6 | 4.6 | 4.7 |
| δP | — | 0 | 0 | 0 | 0 | 0.054 |

In the above table, δP refers to a parameter expressing the temperature characteristic and is defined by the following equation:

$$\delta P = \frac{2(P(t_1) - P(t_2))}{P(t_1) + P(t_2)} \times \frac{100}{t_1 - t_2}$$

In this equation, P(t) represents a pitch length at t° C. and t represents temperature.

As described above, liquid crystal compositions containing the compound of the present invention have characteristics that the exhibited pitch is very short and change in the pitch length with temperature change hardly occurs; thus it has been found that the compound of the present invention is a very good agent for adjusting the pitch of liquid crystal compositions.

EXAMPLE 3

Preparation of (R)-4-octyloxybiphenyl-4'-carboxylic acid 1-(2-pyridyl)ethyl ester (i) Preparation of (R)-1-(2-pyridyl)ethanol Example 1 was repeated except that 3-acetylpyridine used in Example 1 was replaced by 2-acetylpyridine to obtain (R)-1-(2-pyridyl)ethanol. According to a high-speed liquid chromatography using an optical resolution column (CHIRAL CEL OB made by Daicel K. K.), its optical purity was 95% ee or higher.

(ii) Preparation of (R)-4-octyloxybiphenyl-4'-carboxylic acid 1-(2-pyridyl)ethyl ester (a compound of the formula (I) wherein m=n=1,

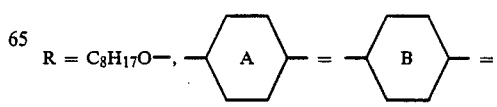

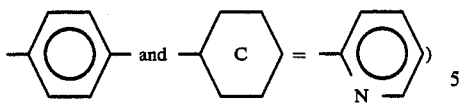

(R)-1-(2-pyridyl)ethanol (2.0 g) obtained in the above item (i), 4-octyloxybiphenyl-4'-carboxylic acid (5.3 g), dicyclohexylcarbodiimide (5.7 g) and dimethylaminopyridine (0.2 g) were dissolved in methylene chloride (100 ml), followed by agitating the solution for 15 hours, thereafter filtering off insolubles, washing the filtrate with water, concentrating it and recrystallizing from a mixed solvent of heptane-toluene to obtain (R)-4-octyloxybiphenyl-4'-carboxylic acid 1-(2-pyridyl)ethyl ester (2.8 g). M.P.: 70.5–71.2° C. Specific angle of rotation $[a]_D^{25} = -83.5°$ (c=1.1, CHCl$_3$). Further, this product was confirmed to be the captioned compound according to NMR spectra.

EXAMPLE 4 (USE EXAMPLE 2)

To a nematic liquid crystal composition (commercially available ZLI-1132 made by Merck Company) was added the compound of Example 3 of the present invention

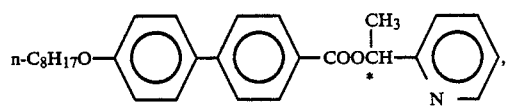

in an amount of 1% by weight to prepare a chiral nematic liquid crystal composition, followed by filling this composition in a wedge type cell subjected to a parallel treatment and observing the resulting cell under a polarizing microscope. As a result, the following helical pitch and temperature characteristic δP were observed:

| Temperature (°C.) | 20 | 25 | 30 | 40 | 50 | 60 |
|---|---|---|---|---|---|---|
| Pitch length (μm) | 8.7 | 8.6 | 8.5 | 8.4 | 8.4 | 8.2 |
| δP | — | −0.231 | −0.233 | −0.175 | −0.157 | −0.148 |

EXAMPLE 5 (USE EXAMPLE 3)

A liquid crystal composition consisting of the following liquid crystal compounds was prepared:

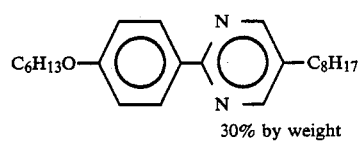

30% by weight

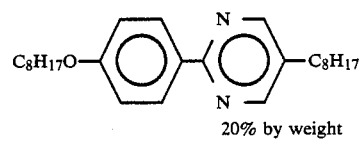

20% by weight

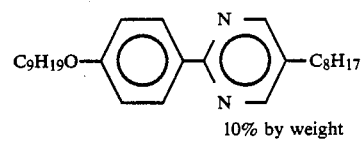

10% by weight

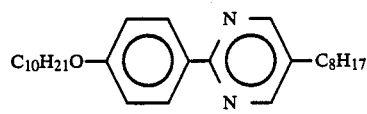

10% by weight

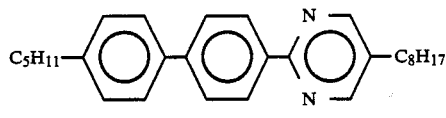

20% by weight

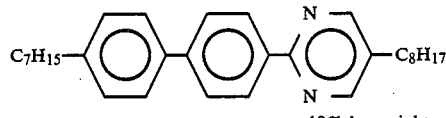

10% by weight

The phase transition points of the above liquid crystal composition were as follows:

$$Cr \xrightarrow{4° C.} Sc \xrightarrow{65° C.} S_A \xrightarrow{79° C.} N \xrightarrow{90° C.} I$$

To this liquid crystal composition was added the compound of Example 3

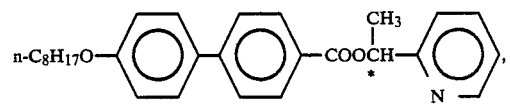

in an amount of 5% by weight to prepare a liquid crystal composition. Its phase transition points were as follows:

$$Sc* \xrightarrow{47° C.} S_A \xrightarrow{78° C.} Ch \xrightarrow{87° C.} I$$

Further, this liquid crystal composition was filled in a cell of 2 um thickness provided with transparent electrodes, followed by placing the resulting liquid crystal element between a polarizer and a detector crossed to each other and impressing a voltage. As a result, change in the intensity of transmitted light was confirmed at 47° C. or lower; thus the composition was found to exhibit a ferroelectric liquid crystal phase.

EXAMPLE 6

Preparation of (R)-4-(4-butylphenyl)cyclohexylcarboxylic acid 1-(4-pyridyl)ethyl ester (i) Preparation of (R)-1-(4-pyridyl)ethanol Example 1 was repeated except that 3-acetylpyridine used in Example 1 was replaced by 4-acetylpyridine to obtain (R)-1-(4-pyridyl)ethanol. $[a]_D^{25} = +32.4°$ (c=1.0, EtOH). Its optical purity was 99% ee or higher according to a high-speed liquid chromatography using an optical resolution column (CHIRAL CEL OB made by Daicel K. K.).

(ii) Preparation of
(R)-4-(4-butylphenyl)cyclohexylcarboxylic acid
1-(4-pyridyl)ethyl ester (a) compound of the formula (I) wherein m=n=1,

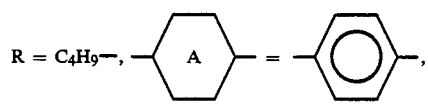

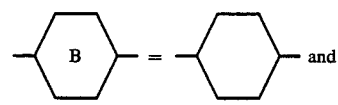

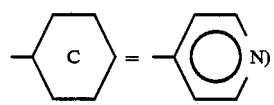

(R)-1-(4-pyridyl)ethanol obtained in the above item (i) (2.0g), 4-(4-butylphenyl)cyclohexylcarboxylic acid (5.0 g), dicyclohexylcarbodiimide (5.7 g) and dimethylaminopyridine (0.2 g) were dissolved in methylene chloride (100 ml), followed by agitating the solution for 15 hours, thereafter filtering off insolubles, washing the filtrate with water, concentrating it and recrystallizing from a mixed solvent of heptane-toluene to obtain (R)-4-(4-butylphenyl)cyclohexylcarboxylic acid 1-(4-pyridyl)ethyl ester (2.1 g).

What we claim is:

1. An optically active pyridylethanol derivative expressed by the formula

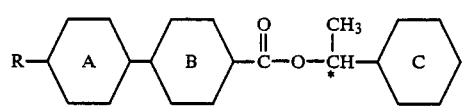

wherein R represents alkyl or alkoxy each of 1 to 20 carbon atoms,

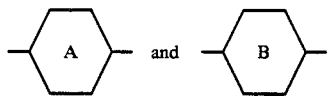

each independently represent

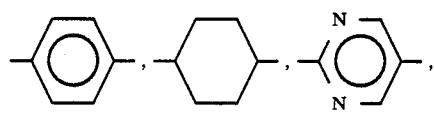

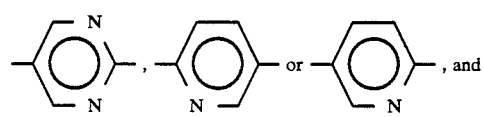

represents 2-pyridyl, 3-pyridyl or 4-pyridyl.

2. An optically active pyridylethanol derivative according to claim 1 wherein said

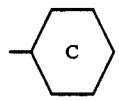

represents 2-pyridyl.

3. An optically active pyridylethanol derivative according to claim 1 wherein said

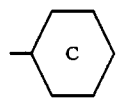

represents 3-pyridyl.

4. An optically active pyridylethanol derivative according to claim 1 wherein said

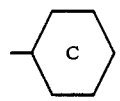

represents 4-pyridyl.

5. An optically active pyridylethanol derivative according to claim 1 wherein said

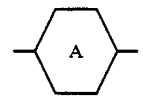

represents

6. An optically active pyridylethanol derivative according to claim 1 wherein said

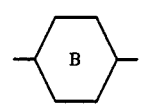

represents

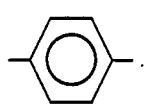

7. An optically active pyridylethanol derivative according to claim 1 wherein said

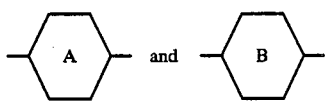 both represent 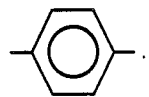.
8. A liquid crystal composition comprising at least two components at least one of which is an optically active pyridylethanol derivative as set forth in claim 1.
* * * * *